US008496634B2

(12) United States Patent
Wallace

(10) Patent No.: US 8,496,634 B2
(45) Date of Patent: Jul. 30, 2013

(54) COLONIC LAVAGE CATHETER

(75) Inventor: Michael B. Wallace, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 242 days.

(21) Appl. No.: 12/835,397

(22) Filed: Jul. 13, 2010

(65) Prior Publication Data

US 2011/0034865 A1 Feb. 10, 2011

Related U.S. Application Data

(60) Provisional application No. 61/226,182, filed on Jul. 16, 2009.

(51) Int. Cl.
*A61M 31/00* (2006.01)
*A61M 1/00* (2006.01)
*A61M 3/02* (2006.01)
*A61F 5/44* (2006.01)

(52) U.S. Cl.
USPC ................ 604/275; 604/39; 604/27; 604/328

(58) Field of Classification Search
USPC ................... 604/275–279, 327–332, 334, 27, 604/35, 39
See application file for complete search history.

(56) References Cited

U.S. PATENT DOCUMENTS

| | | | |
|---|---|---|---|
| 2,603,217 A * | 7/1952 | McShirley | 604/265 |
| 4,842,583 A * | 6/1989 | Majlessi | 604/43 |
| 5,083,561 A | 1/1992 | Russo | |
| 5,300,022 A * | 4/1994 | Klapper et al. | 604/35 |
| 5,775,325 A | 7/1998 | Russo | |
| 6,190,365 B1 * | 2/2001 | Abbott et al. | 604/279 |
| 6,227,200 B1 | 5/2001 | Crump et al. | |
| 6,589,216 B1 * | 7/2003 | Abbott et al. | 604/279 |
| 6,918,517 B2 * | 7/2005 | Shu | 222/568 |
| 7,186,243 B1 * | 3/2007 | Mezzoli | 604/279 |
| 8,057,448 B2 * | 11/2011 | Williams et al. | 604/319 |
| 8,167,853 B2 * | 5/2012 | Wong | 604/279 |
| 2001/0044600 A1 | 11/2001 | Elkins | |
| 2007/0106174 A1 * | 5/2007 | Sanders et al. | 600/563 |
| 2007/0270767 A1 * | 11/2007 | Khieu et al. | 604/264 |
| 2011/0071440 A1 * | 3/2011 | Torrance et al. | 601/2 |

OTHER PUBLICATIONS

International Search Report for PCT/US2010/041827, dated Mar. 4, 2011.
Written Opinion for PCT/US2010/041827, dated Mar. 4, 2011.

* cited by examiner

*Primary Examiner* — Laura A Bouchelle
*Assistant Examiner* — Rebecca E Eisenberg
(74) *Attorney, Agent, or Firm* — Marshall, Gerstein & Borun LLP

(57) ABSTRACT

A colonic lavage catheter includes a head attached at an end of a suction tube and having both rearward and lateral fluid discharge openings. A pair of tubes extend along the suction tube with their ends attached to the head to place the rearward and lateral fluid discharge openings in fluid communication with a source of pressurized fluid. The suction tube includes a plurality of suction orifices through the outer wall along its length proximate the catheter head. A cleaning process may be performed by inserting the catheter head into the colon and then discharging fluid through the rearward openings to advance the catheter. At points along the colon, pressurized fluid may be discharged through the lateral discharge openings to lavage the adjacent walls of the colon, with suction being applied to draw the dislodged material into the suction tube through the suction orifices.

20 Claims, 2 Drawing Sheets

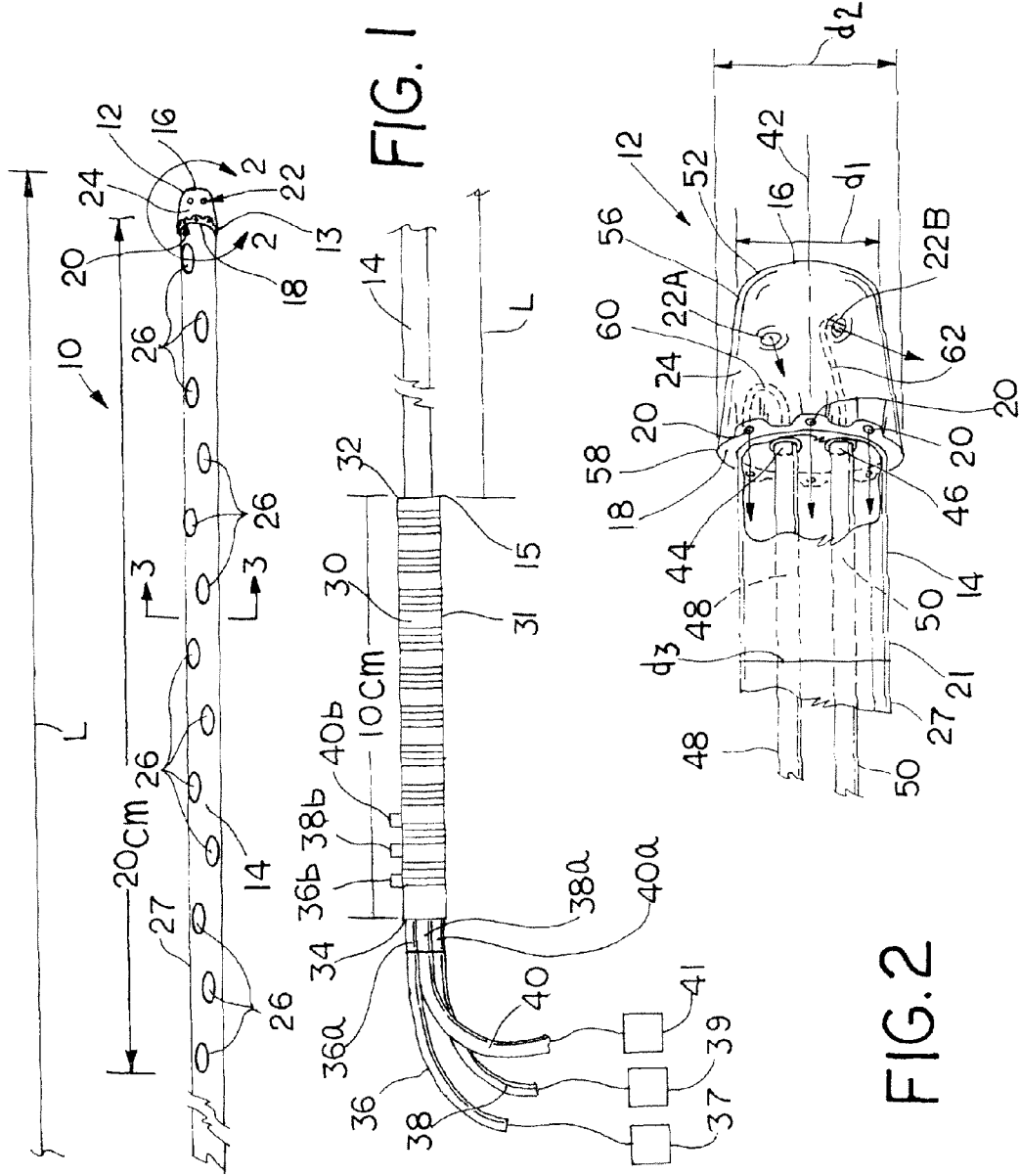

COLONIC LAVAGE CATHETER

FIELD OF THE DISCLOSURE

The present disclosure generally relates to preparation of the colon prior to colon examination by endoscope or other methods and, more particularly, to a colonic lavage catheter having a head with rearward fluid discharge for advancing the catheter in the colon and lateral fluid discharge to lavage the colon, and a suction tube having orifices for evacuation of semi-solid and liquid stool.

BACKGROUND

Colon examinations are performed using an endoscope or other imaging methods such as computed tomography (CT) or magnetic resonance (MR) colonography. Regardless of the examination method, the colon must be cleaned out prior to the examination so that the colon walls are visible and polyps and other irregularities within the colon can be detected. In many cases, the cleaning process involves a large volume purge from the colon, and the patient may be required to take pills or a cathartic liquid to facilitate the process.

To some patients, enduring the bowel preparation is the most unpleasant part of the examination because the process can be time-consuming and uncomfortable. Moreover, some patients are unable to perform a complete purge despite using their best efforts. In other cases, the patients may simply be unable to perform the necessary pre-examination bowel preparation for a variety of other reasons. Therefore, a need exists for a device and a procedure for rapid cleaning of the colon in preparation for a colon examination that reduces or eliminates the need for a large volume purge, thereby allowing the patient to come to the examination with minimal preparation and have the device perform the necessary cleaning of the colon.

SUMMARY

In accordance with an aspect of the invention, a colonic lavage catheter includes a catheter head comprising a frusto-conical body with a lateral surface, a forward end having a first diameter and a rearward end having a second diameter that is greater than the first diameter, a plurality of rearward discharge openings proximate the rearward end of the body and oriented to discharge a fluid in the rearward direction, a plurality of lateral discharge opening through the lateral surface of the body and oriented to discharge a fluid laterally from the body, a first inlet through the rearward end of the body in fluid communication with the rearward discharge openings, and a second inlet through the rearward end of the body in fluid communication with the lateral discharge openings. The device further includes a first fluid supply tube connected to the first inlet to place the first fluid supply tube in fluid communication with the rearward discharge openings, a second fluid supply tube connected to the second inlet to place the second fluid supply tube in fluid communication with the lateral discharge openings, and a suction tube connected to the rearward end of the body and having a plurality of suction orifices through a portion of an outer wall of the suction tube proximate the body such that loose matter proximate the suction orifices is drawn into the suction tube when a vacuum is created within the suction tube.

In accordance with one or more preferred forms, the catheter head preferably includes first internal channels placing the first outlet in fluid communication with the rearward discharge openings and second internal channels placing the second inlet in fluid communication with the lateral discharge openings. The catheter head may have a longitudinal axis and the forward end and rearward end may be perpendicular or generally perpendicular to the longitudinal axis. The rearward discharge openings may be oriented to discharge fluid from the first fluid supply tube parallel to the longitudinal axis of the catheter head, and/or the rearward discharge openings may be oriented to discharge fluid from the first fluid supply tube at an acute angle with respect to the longitudinal axis of the catheter head. Further, the lateral discharge openings may be asymmetrically oriented with respect to the longitudinal axis of the catheter head so that a net force is applied to the catheter head perpendicular to the longitudinal axis when fluid is discharged from the lateral discharge openings, and/or at least one of the lateral discharge openings may be oriented to discharge fluid in a discharge direction that does not intersect the longitudinal axis of the catheter head.

Still further, a first lateral discharge opening may discharge fluid in a first discharge direction and a second lateral discharge opening may discharge fluid in a second discharge direction, with the first discharge direction being more rearward than the second discharge direction. The first and second fluid supply tubes may disposed within the suction tube, or contained within a wall of the suction tube. A first control mechanism may be operatively connected to the first fluid supply tube, a second control mechanism may be operatively connected to the second fluid supply tube, and a third control mechanism may be operatively connected to the suction tube, and the first, second and third control mechanisms may be operable to independently discharge fluids from the rearward and lateral discharge openings and apply suction through the suction orifices of the suction tube.

In accordance with another aspect, a colonic lavage catheter comprises a catheter head having a plurality of rearward discharge openings oriented to discharge a fluid in the rearward direction, and a plurality of lateral discharge opening oriented to discharge a fluid laterally from the body, a first fluid supply tube operatively connected to the rearward discharge openings to place the rearward discharge openings in fluid communication with a first pressurized fluid source, a second fluid supply tube connected to the lateral discharge openings to place the lateral discharge openings in fluid communication with a second pressurized fluid source, and a suction tube connected to a rearward end of the catheter head and having a plurality of suction orifices through a portion of an outer wall of the suction tube proximate the catheter head such that loose matter proximate the suction orifices is drawn into the suction tube when a vacuum is created by a vacuum source connected to the suction tube.

In accordance with additional preferred forms, the plurality of suction orifices through a portion of the outer wall of the suction tube are spaced apart, the spacing creating an alternating pattern when viewed at an angle perpendicular to the longitudinal axis of the suction tube. The lateral discharge openings may be asymmetrically oriented with respect to each other to promote a lateral movement of the catheter head when fluid is discharged from the lateral discharge openings. The discharge of fluid from a first lateral discharge opening may be randomized with respect to the discharge of fluid from a second lateral discharge opening to ensure that all parts of the colon walls are sprayed with pressurized fluid. The first, second and third control mechanisms may be operable to discharge fluids from the rearward and lateral discharge openings and apply suction through the suction orifices of the suction tube at different flow rates and pressures. Still further, the rearward discharge openings may be circumferentially spaced around the rearward end or otherwise symmetrically arranged about the catheter head so that minimal or no force is applied perpendicular to the longitudinal axis of the catheter head during rearward fluid discharge. In accordance with an exemplary form, such an arrangement may prevent unnecessary or undesirable lateral movement of the catheter head.

In accordance with a further exemplary aspect, a method is disclosed for performing a rapid cleaning procedure of the colon using a colonic lavage catheter having a catheter head with a plurality of rearward fluid discharge openings and a plurality of lateral fluid discharge openings, and a suction tube attached at a rearward end of the catheter head and having a plurality of suction orifices proximate the catheter head. The method comprises inserting the catheter head into the colon, inserting additional portions of the suction tube into the colon, discharging pressurized liquid through the rearward discharge openings of the catheter head to create a force advancing the catheter within the colon, discharging pressurized liquid through the lateral discharge openings of the catheter head to lavage the walls of the colon, and applying suction through the suction orifices of the suction tube to draw semi-solid and liquid material proximate the suction orifices into the suction tube to evacuate material dislodged from the colon walls from the colon.

BRIEF DESCRIPTION OF THE DRAWINGS

FIG. 1 is a side view of an embodiment of a colonic lavage catheter in accordance with the present disclosure;

FIG. 2 is an enlarged view of the head of the colonic lavage catheter of FIG. 1 at the area indicated by line 2-2;

DETAILED DESCRIPTION OF THE DISCLOSURE

Figure 3:
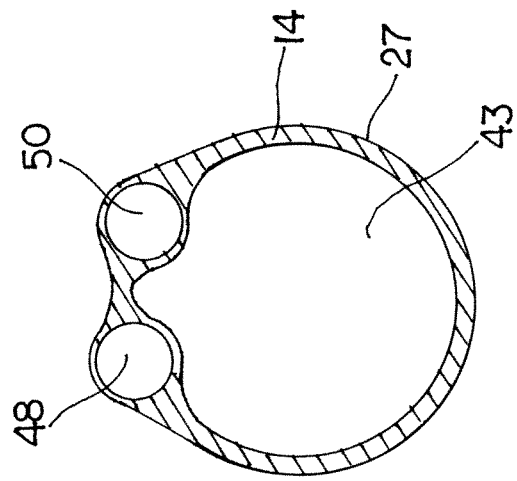
FIG. 3 is a cross-sectional view of the colonic lavage catheter taken through line 3-3 of FIG. 1 illustrating an arrangement of the first and second fluid supply tubes and the suction tube.

Although the following text sets forth a detailed description of numerous different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____'is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

In order to perform rapid cleaning of the colon and reduce the amount of preparation required of patients prior to a colon examination, a colonic lavage catheter is provided to lavage the colon and evacuate the dislodged waste from the colon. In one embodiment, the colonic lavage catheter may include a catheter head attached at an end of a suction tube and having both rearward fluid discharge openings and lateral fluid discharge openings. A pair of fluid supply tubes may extend along the suction tube, either internal or external to the suction tube, with their ends being attached to inlets at the rearward end of the catheter head to place the fluid supply tubes in fluid communication with the rearward and lateral fluid discharge openings. The suction tube may include a plurality of suction orifices through the outer wall of the suction tube along its length proximate the catheter head. The suction orifices may be dimensioned to allow semi-solid and liquid stool to enter the suction tube when a vacuum is applied. The rapid cleaning process may be performed by first inserting the catheter head into the colon, and then discharging pressurized fluid from one of the fluid supply tubes through the rearward openings of the catheter head to advance the catheter within the colon. At various points along the colon, pressurized fluid from the other fluid supply tube may be discharged through the lateral discharge openings of the catheter head to lavage the adjacent walls of the colon, with suction being applied to draw the dislodged material into the suction tube through the suction orifices.

FIG. 1 illustrates one embodiment of a colonic lavage catheter 10 in accordance with the present disclosure having a catheter head 12 attached at a forward end 13 of a suction tube 14. The illustration of the colonic lavage catheter 10 has been divided into two sections or pieces in order to fit on the page. The catheter head 12 may have a generally frustoconical shape to facilitate insertion into and advancement within the colon, with a forward end 16 having a diameter $d_1$ that is smaller than a diameter $d_2$ of a rearward end 18 of the catheter head 12. The rearward end 18 of the catheter head 12 is attached to the forward end 13 of the suction tube 14. The diameter of the rearward end 18 may also be larger than an outer diameter $d_3$ of the suction tube 14. As will be discussed further hereinafter, the catheter head 12 may include a plurality of rearward fluid discharge openings 20 proximate the rearward end 18, and a plurality of lateral fluid discharge openings 22 through a lateral surface 24 of the catheter head 12 for discharging fluid outwardly from the catheter head 12.

The suction tube 14 preferably has a length L that allows for the insertion of the catheter 10 into the entire length of the colon, which length may be approximately 100-150 centimeters. Longer or shorter lengths may [prove suitable. A forward portion 21 of the suction tube 14 generally proximate or adjacent to the catheter head 12 may include a plurality of suction orifices 26 through an outer wall 27 of the suction tube 14 to allow the semi-solid and/or liquid waste to be evacuated from the colon of a patient into the suction tube 14 when suction is applied.

The suction orifices 26 may be dimensioned as large as practical relative to the outer diameter of the suction tube 14 to maximize the size of the material that can be drawn into the suction tube 14 while maintaining a necessary amount of rigidity for the forward portion 21 of the suction tube 14. For example, a suction tube 14 having an outer diameter of 1.2-1.3 centimeters may have suction orifices 26 in the range of 5-8 millimeters. Similar considerations may be relevant to determining the number and positioning of the suction orifices 26 on the suction tube 14. As shown in FIG. 2, the suction orifices 26 may be placed in a pattern. For example, the suction orifices may be spaced apart along the length L of the relevant portion of the suction tube 14. Further, the suction orifices 26 may be spaced apart around a circumference of the suction tube 14. In the example of FIG. 2, adjacent suction orifices 26 are not aligned with one another, but instead are offset circumferentially in an alternating pattern.

The suction tube 14 may be fabricated from any appropriate material typically used in medical devices such as colonoscopes, catheters, nasogastric tubes and the like that are inserted into patients. Preferably the selected material will be flexible while still having sufficient strength for insertion and advancement of the catheter 10 into the colon without collapsing and thereby constricting the passageway of the suction tube 14 when the anticipated amounts external pressure are exerted on the tube 14 or when the suction is applied through the tube 14. Examples of materials from which the suction tube 14 may be fabricated include silicone rubber, polypropylene (PP), ethyl vinyl alcohol (EVA), polyethylene, polyester (PE), nylon (poly amide), and/or composites thereof. Still other materials may prove suitable.

Preferably, a connection portion 30 is provided at or adjacent to a proximal or rearward end 15 of the suction tube 14 (i.e., the rearward end 15 is opposite the forward end 13). The connection portion 30 may include a handle portion 31 suitable for gripping by a user. The connection portion 30 facilitates the connection of sources of pressurized fluids and suction to the catheter 10. The connection portion 30 includes a forward end 32 that is configured to receive the rearward end 15 of the suction tube 14, and the connection portion 30 includes a rearward end 34 having a plurality of inlets. For example, the connection portion 30 may include a first inlet 36a for connecting a first fluid supply tube 36, a second inlet 38a for connecting a second fluid supply tube 38, and a third inlet 40a for connecting a suction supply tube 40. In turn, the first and second supply tubes 36 and 38 are connected to a first fluid source 37 and a second fluid source 39, respectively. Further, the third supply tube is connected to a suction source 41. Once connected to the rearward end 34 of the connection portion 30 via the appropriate inlets 36a and 38a, the tubes 36, 38 are placed in fluid communication with corresponding fluid supply tubes 48 and 50, respectively (illustrated in FIG. 2). As shown in FIG. 2, the supply tubes 48 and 50 extend through the suction tube 14 to the catheter head 12, such that flow communication is provided from the source 37 to the supply tube 48, and from the source 39 to the supply tube 50. Further, by virtue of the connection between the supply tube 40 and the inlet 40a, an interior portion 43 of the suction tube 14 is in flow communication with the suction source 41.

As outlined above, the fluid supply tubes 36, 38 are or may be may be operatively coupled to the sources 37 and 39 of pressurized fluid, so that the pressurized fluid may be discharged from the rearward discharge openings 20, the lateral discharge openings 22, or both, as necessary to advance the catheter 10 and lavage the colon. The sources 37 and 39 may be separate from one another, such as independently operable pumps or other suitable supply sources. Alternatively, the sources 37 and 39 may be combined into a single unit. The connection portion 30 may be provided with controls 36b, 38b and 40b, which may take the form of triggers or other suitable control mechanisms. The controls 36b and 38b control fluid flow through the supply tubes 48 and 50 to the catheter head 12, while the control 40b controls suction within the suction tube 14. The controls allow the medical professional to discharge pressurized fluid and operate the suction in the suction tube 14 as necessary for the rapid cleaning and evacuation process.

Preferably, the pressurized fluid source 37 and 39, supply tubes 36, 38, 48 and 50, as well as the openings 20, 22, may be configured to discharge the fluid with sufficient pressure and velocity to lavage the colon without damaging the colon walls. Still preferably, the flow rate of supplied fluid as well as the pressure through the rearward discharge openings 20 may be different than through the lateral discharge openings 22.

Of course, other arrangements for connecting pressurized fluids and suction sources to the catheter 10 and controlling the discharge of fluids and the application of suction will be apparent to those skilled in the art and are contemplated by the inventor as having use with colonic lavage catheters in accordance with the present disclosure.

Referring to FIG. 2, the catheter head 12 is shown in greater detail. In the illustrated embodiment, the frustoconical head 12 may include a tip 52 which may be either generally planar or rounded. The head further may include rounded edges 56 and 58 at the intersections of the forward end 16 and the rearward end 18 with the lateral surface 24 to facilitate insertion of the catheter 10 into the colon and movement therewithin without puncturing or abrading the inner walls of the colon. The catheter head 12 may have a longitudinal axis 42 that may be approximately coincident with a longitudinal axis of the suction tube 14 attached thereto. The rearward end 18 of the catheter head 12 may be generally planar and perpendicular to the longitudinal axis 42, and the tip 52 may be generally symmetric relative to the axis 42.

The rearward end 18 is configured for attachment to the suction tube 14, and may be recessed to receive the end of the suction tube 14 as shown. However, other attachment mechanisms are also contemplated by the inventor and will be apparent to those skilled in the art. The rearward end 16 may also include first and second inlets 44, 46, which receive the supply tubes 48, 50, respectively. The supply tubes 48, 50 are in fluid communication with the fluid supply tubes 36, 38, respectively, to supply pressurized fluid to the catheter head 12. The first inlet 44 places the first pressurized fluid tube 48 in fluid communication with the rearward discharge openings 20 via a first set of internal channels 60 (only one of which is illustrated schematically in FIG. 2), and the second inlet 46 places the second pressurized fluid tube 50 in fluid communication with the lateral discharge openings 22 via a second set of internal channels 62 (one of which is illustrated schematically in FIG. 2). Various configurations of the catheter head 12 and internal channels 60, 62 are contemplated for connecting the inlets 44, 46 to the openings 20, 22, respectively. For example, the catheter head 12 may be generally hollow, and the internal channels 60, 62 may be provided in the form of interconnected tubes extending from the singular inlets 44, 46 and branching off to each of the plurality of openings 20, 22. In another embodiment, the catheter head 12 may be integrally formed as a single unitary component, such as by injection molding, with the inlets 44, 46, the internal channels 60, 62, and the openings 20, 22 being formed during the molding process. As a further embodiment, the catheter head 12 may have a multi-piece construction with the internal channels 60, 62 being wholly or partially formed in the gaps between the pieces when the catheter head 12 is assembled. Of course, additional methods for forming the catheter head 12 and placing the inlets 44, 46 in fluid communication with the openings 20, 22 will be apparent to those skilled in the art and are contemplated by the inventor.

A cross-section of a configuration of the suction tube 14 and pressurized fluid tubes 48, 50 is shown FIG. 3. In the illustrated embodiment, the pressurized fluid tubes 48, 50 are disposed in the interior 43 of the suction tube 14. The suction tube 14 and pressurized fluid tubes 48, 50 may be dimensioned so that the tubes 48, 50 fit within the interior 43 of the suction tube 14 with sufficient additional space for the evacuated waste from the colon to pass without creating obstructions within the suction tube 14. For example, the suction tube 14 may have an outer diameter comparable to that of currently used endoscopes, such as in the range of approximately 1.0-1.5 centimeters. Correspondingly, the fluid tubes 48, 50 may have outer diameters in the range of approximately 2.5-4.0 millimeter. To further ensure sufficient space within the suction tube 14, the fluid tubes 48, 50 may be attached to the inner surface of the suction tube 14. As shown, the fluid tubes 48, 50 may be positioned proximate each other. However, the fluid tubes 48, 50 may be positioned at other locations within the suction tube 14 to provide passage space and to avoid obstructing the suction orifices 26. Alternatively, the space within the suction tube 14 may be maximized by disposing the fluid tubes 48, 50 external to the suction tube 14, possibly with the fluid tubes 48, 50 being attached to the outer surface of the suction tube 14.

Figure 4:
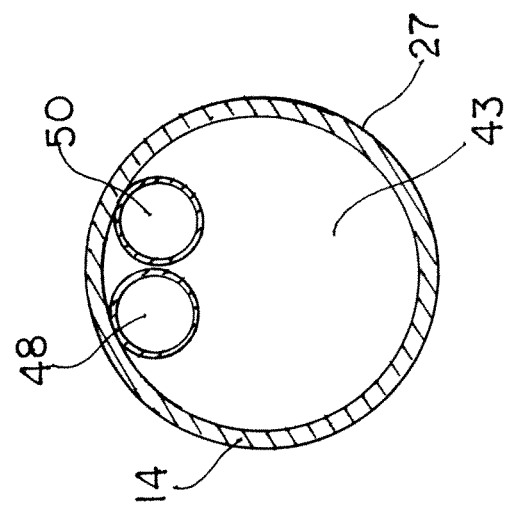
FIG. 4 is a cross-sectional view of an alternate embodiment of the colonic lavage catheter of FIG. 1 with suction tube and fluid supply tubes integrally formed as a single component.

In a further alternative shown in FIG. 4, the suction tube 14 and fluid tubes 48, 50 may be integrally formed as a single component having three separate passages for fluid flow. The integral tube may be formed by extrusion or other appropriate methods, and may provide a large passage in the suction tube 14 without having the fluid tubes 48, 50 dispose wholly external to the suction tube 14. In any of these and other arrangements, the suction tube 14, the fluid tubes 48, 50 and the catheter head 12 will be configured as necessary for attachment of the suction tube 14 at the rearward end 18 of the catheter head 12 and the fluid tubes 48, 50 to the inlets 44, 46, respectively.

Returning to FIG. 2, arrows illustrate the discharge of fluid from the discharge openings 20, 22. The rearward discharge openings 20 discharge fluid generally in the rearward direction, and opposite the direction of movement of the catheter 10 as the catheter 10 is inserted into the colon. The direction of the rearward discharge may be parallel to the longitudinal axis 42 of the catheter head 12, or at a small acute angle with respect to the longitudinal axis 42 as necessary to create a force tending to move the catheter head 12 in the forward direction to assist with advancement of the catheter 10 into the colon. To prevent unnecessary or undesirable lateral movement of the catheter head 12, the rearward discharge openings 20 may be circumferentially spaced around the rearward end 18 or otherwise symmetrically arranged so that minimal or no force is applied perpendicular to the longitudinal axis 42 of the catheter head 12 during the rearward fluid discharge.

The lateral discharge openings 22 are oriented to discharge fluid outwardly from the lateral surface 24 of the catheter head 12 to lavage the colon walls and break up solid waste within the colon. The desired number of lateral discharge openings 22 may be distributed circumferentially about the lateral surface 24, and generally have a greater component of force perpendicular to the longitudinal axis 42 of the catheter head 12 than the rearward discharge openings 20. The greater outward force is necessary to impact and break loose the solid waste within the colon. At the same time, the rearward component of the lateral fluid discharge may assist in directing the dislodged matter rearwardly toward the suction orifices 26 of the suction tube 14.

FIG. 2 further illustrates that the lateral discharge openings 22 may have an asymmetrical configuration with respect to each other and to the longitudinal axis 42 of the catheter head 12. The asymmetrical orientation of the lateral discharge openings 22 promotes lateral movement of the catheter head 12 and a random firing pattern to ensure that all parts of the colon walls are sprayed with pressurized fluid. A first lateral discharge opening 22A may have a first orientation with respect to the longitudinal axis 42 of the catheter head 12 having a substantial downward component, and with an angle of discharge that does not intersect the longitudinal axis 42 of the catheter head 12. A second lateral discharge opening 22B may have a second orientation with a greater lateral component, and with a discharge angle that may or may not intersect the longitudinal axis 42. Additional lateral discharge openings 22 are provided about the lateral surface 25 with varying discharge angles to create a net lateral force perpendicular to the longitudinal axis 42 causing the catheter head 12 to move within the colon and distribute the pressurized fluid across the entire inner wall of the colon for complete cleaning. Those skilled in the art will understand that many different combinations of lateral discharge openings 22 having asymmetrical discharge configurations for lateral movement of the catheter head 12 and randomized and complete spraying of the colon walls may be implemented in the catheter, and such combinations are contemplated by the inventor.

With the catheter 10 as illustrated and described herein, the rapid cleaning process begins with the catheter head 12 being inserted into the colon. As the suction tube 14 is fed into the colon, pressurized fluid is selectively provided through the first fluid tubes 36, 48 and discharged through the rearward discharge openings 20 to create a rearward force at the catheter head 12 that assists in advancing the catheter 10 into the colon. As the catheter 10 is advanced within the colon, pressurized fluid is provided periodically through the second fluid tubes 38, 50 and discharged through the lateral discharge openings 22 to lavage the colon walls. The asymmetric configuration of the lateral discharge openings 22 causes the catheter head 12 to move within the colon to ensure that all portions of the colon wall are cleansed. At the time of the lateral discharge or shortly thereafter, suction is applied through the suction supply tube 40 to the suction tube 14 to draw the dislodged waste and liquid into the suction orifices 26 for removal through the suction tube 14. The rapid cleaning process continues until the necessary length of the catheter 10 is inserted into the colon to ensure complete cleansing of the colon. The catheter 10 is then withdrawn from the colon, with additional lateral fluid discharge and suction being applied if necessary.

The colonic lavage catheter 10 in accordance with the present disclosure provides a simple device for performing a rapid cleaning of the colon in preparation for colon examinations or other procedures. The catheter 10 facilitates complete cleaning of the colon without the necessity of viewing the interior of the colon with a colonoscope. Moreover, in providing both the discharge of fluid and the application of suction, the cleansing may be performed with minimal leakage of dislodged waste from the colon. The need for a large volume purge by a patient in preparation for the procedure may be wholly or completely eliminated. The ability to prepare the patient at the time of the procedure can result in fewer aborted procedures, and help ensure accurate and complete results when the procedures are performed.

In light of the foregoing, the description of the present disclosure should be understood as merely providing examples of the present invention and, thus, variations that do not depart from the gist of the invention are intended to be within the scope of the invention.

What is claimed:
1. A colonic lavage catheter, comprising:
 a catheter head comprising:

a frustoconical body with a lateral surface, a forward end having a first diameter and a rearward end having a second diameter that is greater than the first diameter, a plurality of rearward discharge openings proximate the rearward end of the body and oriented to discharge a fluid in the rearward direction, a plurality of lateral discharge opening through the lateral surface of the body and oriented to discharge a fluid laterally from the body, a first inlet through the rearward end of the body in fluid communication with the rearward discharge openings, and a second inlet through the rearward end of the body in fluid communication with the lateral discharge openings;

a first fluid supply tube connected to the first inlet to place the first fluid supply tube in fluid communication with the rearward discharge openings;

a second fluid supply tube connected to the second inlet to place the second fluid supply tube in fluid communication with the lateral discharge openings; and a suction tube connected to the rearward end of the body and having a plurality of suction orifices through a portion of an outer wall of the suction tube proximate the body such that loose matter proximate the suction orifices is drawn into the suction tube when a vacuum is created within the suction tube.

2. The colonic lavage catheter of claim 1, wherein the catheter head has a longitudinal axis and the forward end and rearward end are perpendicular to the longitudinal axis.

3. The colonic lavage catheter of claim 2, wherein the lateral discharge openings are asymmetrically oriented with respect to the longitudinal axis of the catheter head so that a net force is applied to the catheter head perpendicular to the longitudinal axis when fluid is discharged from the lateral discharge openings.

4. The colonic lavage catheter of claim 2, wherein at least one of the lateral discharge openings discharges fluid in a discharge direction that does not intersect the longitudinal axis of the catheter head.

5. The colonic lavage catheter of claim 1, wherein the first and second fluid supply tubes are disposed within the suction tube.

6. A colonic lavage catheter comprising:

a catheter head comprising:

a frustoconical body with a lateral surface, a forward end having a first diameter and a rearward end having a second diameter that is greater than the first diameter, a plurality of rearward discharge openings proximate the rearward end of the body and oriented to discharge a fluid in the rearward direction, a plurality of lateral discharge opening through the lateral surface of the body and oriented to discharge a fluid laterally from the body, a first inlet through the rearward end of the body in fluid communication with the rearward discharge openings, and a second inlet through the rearward end of the body in fluid communication with the lateral discharge openings;

a first fluid supply tube connected to the first inlet to place the first fluid supply tube in fluid communication with the rearward discharge openings;

a second fluid supply tube connected to the second inlet to place the second fluid supply tube in fluid communication with the lateral discharge openings; and a suction tube connected to the rearward end of the body and having a plurality of suction orifices through a portion of an outer wall of the suction tube proximate the body such that loose matter proximate the suction orifices is drawn into the suction tube when a vacuum is created within the suction tube, wherein the catheter head includes first internal channels placing the first outlet in fluid communication with the rearward discharge openings and second internal channels placing the second inlet in fluid communication with the lateral discharge openings.

7. A colonic lavage catheter comprising:

a catheter head comprising:

a frustoconical body with a lateral surface, a forward end having a first diameter and a rearward end having a second diameter that is greater than the first diameter, a plurality of rearward discharge openings proximate the rearward end of the body and oriented to discharge a fluid in the rearward direction, a plurality of lateral discharge opening through the lateral surface of the body and oriented to discharge a fluid laterally from the body, a first inlet through the rearward end of the body in fluid communication with the rearward discharge openings, and a second inlet through the rearward end of the body in fluid communication with the lateral discharge openings;

a first fluid supply tube connected to the first inlet to place the first fluid supply tube in fluid communication with the rearward discharge openings;

a second fluid supply tube connected to the second inlet to place the second fluid supply tube in fluid communication with the lateral discharge openings; and a suction tube connected to the rearward end of the body and having a plurality of suction orifices through a portion of an outer wall of the suction tube proximate the body such that loose matter proximate the suction orifices is drawn into the suction tube when a vacuum is created within the suction tube, wherein the catheter head has a longitudinal axis and the forward end and rearward end are perpendicular to the longitudinal axis and the rearward discharge openings discharge fluid from the first fluid supply tube parallel to the longitudinal axis of the catheter head.

8. A colonic lavage catheter comprising:

a catheter head comprising:

a frustoconical body with a lateral surface, a forward end having a first diameter and a rearward end having a second diameter that is greater than the first diameter, a plurality of rearward discharge openings proximate the rearward end of the body and oriented to discharge a fluid in the rearward direction, a plurality of lateral discharge opening through the lateral surface of the body and oriented to discharge a fluid laterally from the body, a first inlet through the rearward end of the body in fluid communication with the rearward discharge openings, and a second inlet through the rearward end of the body in fluid communication with the lateral discharge openings;

a first fluid supply tube connected to the first inlet to place the first fluid supply tube in fluid communication with the rearward discharge openings;

a second fluid supply tube connected to the second inlet to place the second fluid supply tube in fluid communication with the lateral discharge openings; and a suction tube connected to the rearward end of the body and having a plurality of suction orifices through a portion of an outer wall of the suction tube proximate the body such that loose matter proximate the suction orifices is drawn into the suction tube when a vacuum is created within the suction tube, wherein the catheter head has a longitudinal axis and the forward end and rearward end are perpendicular to the longitudinal axis and the rearward discharge openings discharge fluid from the first fluid supply tube at an acute angle with respect to the longitudinal axis of the catheter head.

9. A colonic lavage catheter comprising:
a catheter head comprising:
 a frustoconical body with a lateral surface, a forward end having a first diameter and a rearward end having a second diameter that is greater than the first diameter,
 a plurality of rearward discharge openings proximate the rearward end of the body and oriented to discharge a fluid in the rearward direction,
 a plurality of lateral discharge opening through the lateral surface of the body and oriented to discharge a fluid laterally from the body,
 a first inlet through the rearward end of the body in fluid communication with the rearward discharge openings, and
 a second inlet through the rearward end of the body in fluid communication with the lateral discharge openings;
a first fluid supply tube connected to the first inlet to place the first fluid supply tube in fluid communication with the rearward discharge openings;
a second fluid supply tube connected to the second inlet to place the second fluid supply tube in fluid communication with the lateral discharge openings; and
a suction tube connected to the rearward end of the body and having a plurality of suction orifices through a portion of an outer wall of the suction tube proximate the body such that loose matter proximate the suction orifices is drawn into the suction tube when a vacuum is created within the suction tube,
wherein the catheter head has a longitudinal axis and the forward end and rearward end are perpendicular to the longitudinal axis and a first lateral discharge opening discharges fluid in a first discharge direction and a second lateral discharge opening discharges fluid in a second discharge direction, with the first discharge direction being more rearward than the second discharge direction.

10. A colonic lavage catheter comprising:
a catheter head comprising:
 a frustoconical body with a lateral surface, a forward end having a first diameter and a rearward end having a second diameter that is greater than the first diameter,
 a plurality of rearward discharge openings proximate the rearward end of the body and oriented to discharge a fluid in the rearward direction,
 a plurality of lateral discharge opening through the lateral surface of the body and oriented to discharge a fluid laterally from the body,
 a first inlet through the rearward end of the body in fluid communication with the rearward discharge openings, and
 a second inlet through the rearward end of the body in fluid communication with the lateral discharge openings;
a first fluid supply tube connected to the first inlet to place the first fluid supply tube in fluid communication with the rearward discharge openings;
a second fluid supply tube connected to the second inlet to place the second fluid supply tube in fluid communication with the lateral discharge openings;
a suction tube connected to the rearward end of the body and having a plurality of suction orifices through a portion of an outer wall of the suction tube proximate the body such that loose matter proximate the suction orifices is drawn into the suction tube when a vacuum is created within the suction tube;
a first control mechanism operatively connected to the first fluid supply tube;
a second control mechanism operatively connected to the second fluid supply tube; and
a third control mechanism operatively connected to the suction tube,
wherein the first, second and third control mechanisms are operable to independently discharge fluids from the rearward and lateral discharge openings and apply suction through the suction orifices of the suction tube.

11. A colonic lavage catheter, comprising:
a catheter head having a plurality of rearward discharge openings oriented to discharge a fluid in the rearward direction, and a plurality of lateral discharge opening oriented to discharge a fluid laterally from the body;
a first fluid supply tube operatively connected to the rearward discharge openings to place the rearward discharge openings in fluid communication with a first pressurized fluid source;
a second fluid supply tube connected to the lateral discharge openings to place the lateral discharge openings in fluid communication with a second pressurized fluid source; and
a suction tube connected to a rearward end of the catheter head and having a plurality of suction orifices through a portion of an outer wall of the suction tube proximate the catheter head such that loose matter proximate the suction orifices is drawn into the suction tube when a vacuum is created by a vacuum source connected to the suction tube.

12. The colonic lavage catheter of claim 11, wherein the catheter head has a longitudinal axis that is substantially coincident with a longitudinal axis of the suction tube.

13. The colonic lavage catheter of claim 12, wherein the lateral discharge openings are asymmetrically oriented with respect to the longitudinal axis of the catheter head so that a net force is applied to the catheter head perpendicular to the longitudinal axis when fluid is discharged from the lateral discharge openings.

14. The colonic lavage catheter of claim 12, wherein at least one of the lateral discharge openings discharges fluid in a discharge direction that does not intersect the longitudinal axis of the catheter head.

15. The colonic lavage catheter of claim 11, wherein the first and second fluid supply tubes are disposed within the suction tube.

16. A colonic lavage catheter comprising:
a catheter head having a plurality of rearward discharge openings oriented to discharge a fluid in the rearward direction, and a plurality of lateral discharge opening oriented to discharge a fluid laterally from the body;

a first fluid supply tube operatively connected to the rearward discharge openings to place the rearward discharge openings in fluid communication with a first pressurized fluid source;
a second fluid supply tube connected to the lateral discharge openings to place the lateral discharge openings in fluid communication with a second pressurized fluid source; and
a suction tube connected to a rearward end of the catheter head and having a plurality of suction orifices through a portion of an outer wall of the suction tube proximate the catheter head such that loose matter proximate the suction orifices is drawn into the suction tube when a vacuum is created by a vacuum source connected to the suction tube,
wherein the catheter head includes first internal channels placing the first fluid supply tube in fluid communication with the rearward discharge openings and second internal channels placing the second fluid supply tube in fluid communication with the lateral discharge openings.

17. A colonic lavage comprising:
a catheter head having a plurality of rearward discharge openings oriented to discharge a fluid in the rearward direction, and a plurality of lateral discharge opening oriented to discharge a fluid laterally from the body;
a first fluid supply tube operatively connected to the rearward discharge openings to place the rearward discharge openings in fluid communication with a first pressurized fluid source;
a second fluid supply tube connected to the lateral discharge openings to place the lateral discharge openings in fluid communication with a second pressurized fluid source; and
a suction tube connected to a rearward end of the catheter head and having a plurality of suction orifices through a portion of an outer wall of the suction tube proximate the catheter head such that loose matter proximate the suction orifices is drawn into the suction tube when a vacuum is created by a vacuum source connected to the suction tube,
wherein the catheter head has a longitudinal axis that is substantially coincident with a longitudinal axis of the suction tube and the rearward discharge openings discharge fluid from the first fluid supply tube parallel to the longitudinal axis of the catheter head.

18. A colonic lavage comprising:
a catheter head having a plurality of rearward discharge openings oriented to discharge a fluid in the rearward direction, and a plurality of lateral discharge opening oriented to discharge a fluid laterally from the body;
a first fluid supply tube operatively connected to the rearward discharge openings to place the rearward discharge openings in fluid communication with a first pressurized fluid source;
a second fluid supply tube connected to the lateral discharge openings to place the lateral discharge openings in fluid communication with a second pressurized fluid source; and
a suction tube connected to a rearward end of the catheter head and having a plurality of suction orifices through a portion of an outer wall of the suction tube proximate the catheter head such that loose matter proximate the suction orifices is drawn into the suction tube when a vacuum is created by a vacuum source connected to the suction tube,
wherein the catheter head has a longitudinal axis that is substantially coincident with a longitudinal axis of the suction tube and the rearward discharge openings discharge fluid from the first fluid supply tube at an acute angle with respect to the longitudinal axis of the catheter head.

19. A colonic lavage comprising:
a catheter head having a plurality of rearward discharge openings oriented to discharge a fluid in the rearward direction, and a plurality of lateral discharge opening oriented to discharge a fluid laterally from the body;
a first fluid supply tube operatively connected to the rearward discharge openings to place the rearward discharge openings in fluid communication with a first pressurized fluid source;
a second fluid supply tube connected to the lateral discharge openings to place the lateral discharge openings in fluid communication with a second pressurized fluid source; and
a suction tube connected to a rearward end of the catheter head and having a plurality of suction orifices through a portion of an outer wall of the suction tube proximate the catheter head such that loose matter proximate the suction orifices is drawn into the suction tube when a vacuum is created by a vacuum source connected to the suction tube,
wherein the catheter head has a longitudinal axis that is substantially coincident with a longitudinal axis of the suction tube and a first lateral discharge opening discharges fluid in a first discharge direction and a second lateral discharge opening discharges fluid in a second discharge direction, with the first discharge direction being more rearward than the second discharge direction.

20. A colonic lavage catheter comprising:
a catheter head having a plurality of rearward discharge openings oriented to discharge a fluid in the rearward direction, and a plurality of lateral discharge opening oriented to discharge a fluid laterally from the body;
a first fluid supply tube operatively connected to the rearward discharge openings to place the rearward discharge openings in fluid communication with a first pressurized fluid source;
a second fluid supply tube connected to the lateral discharge openings to place the lateral discharge openings in fluid communication with a second pressurized fluid source;
a suction tube connected to a rearward end of the catheter head and having a plurality of suction orifices through a portion of an outer wall of the suction tube proximate the catheter head such that loose matter proximate the suction orifices is drawn into the suction tube when a vacuum is created by a vacuum source connected to the suction tube;
a first control mechanism operatively connected to the first fluid supply tube;
a second control mechanism operatively connected to the second fluid supply tube; and
a third control mechanism operatively connected to the suction tube,
wherein the first, second and third control mechanisms are operable to independently discharge fluids from the rearward and lateral discharge openings and apply suction through the suction orifices of the suction tube.

* * * * *